United States Patent [19]

Lai

[11] 4,347,379

[45] Aug. 31, 1982

[54] SYNTHESIS OF ALPHA-ALKOXYCARBOXYLIC ACIDS

[75] Inventor: John T. Lai, Broadview Heights, Ohio

[73] Assignee: The B. F. Goodrich Company, Akron, Ohio

[21] Appl. No.: 129,000

[22] Filed: Mar. 10, 1980

[51] Int. Cl.$^3$ .............................................. C07C 51/00
[52] U.S. Cl. ................................... 562/495; 564/189; 564/201; 260/399; 564/202; 564/205; 260/405.5; 564/209; 564/210; 260/413; 260/465 D; 260/465.4; 562/426; 562/431; 562/468; 562/470; 562/471; 562/472; 562/500; 562/504; 562/505; 562/507; 562/508; 562/510; 562/581; 562/586; 562/587; 562/588; 562/599; 564/123; 564/161; 564/162; 564/171; 564/174; 564/175; 564/181; 564/188; 564/191
[58] Field of Search ............... 562/470, 588, 471, 431, 562/508, 512, 426, 472, 468, 505, 507, 581, 586, 587, 602, 495, 500, 504, 510, 599; 260/399, 413, 465.4, 465 D, 405.5

[56] References Cited

U.S. PATENT DOCUMENTS

| | | | |
|---|---|---|---|
| 2,490,109 | 12/1949 | Weizmann | 562/588 |
| 2,525,249 | 10/1950 | Weizmann | 562/588 |
| 3,038,002 | 6/1962 | Reeve | 562/470 |
| 3,368,943 | 2/1968 | Gilbert et al. | 562/588 |
| 3,992,432 | 11/1976 | Napier et al. | 260/465.1 |
| 4,167,512 | 9/1979 | Lai | 260/239.3 B |

OTHER PUBLICATIONS

Weizmann et al., J.A.C.S. 70, pp. 1153–1157, (1948).
Starks, Chemtech, Feb. 1980, pp. 110–117, (1980).
Weygand, *Preparative Organic Chemistry*, pp. 868–871, (1972).

*Primary Examiner*—Michael L. Shippen
*Attorney, Agent, or Firm*—Alfred D. Lobo; Nestor W. Shust

[57] ABSTRACT

Numerous alpha-carboxylic acids are prepared in a liquid medium by the reaction of an organic compound having at least one reactive hydroxyl or thiol group, with a monoketone, and a haloform, in the presence of a phase transfer catalyst and an alkali metal hydroxide. The term "alpha-alkoxycarboxylic acids" includes alpha-phenoxycarboxylic acids, alpha-thioalkoxycarboxylic acids and alpha-thiophenoxycarboxylic acids. Specific substituents on the beta carbon atom of an alpha-alkoxycarboxylic (or "2-alkoxycarboxylic") acid reaction product formed in this novel synthesis, are introduced by appropriate choice of the ketone reactant; alkoxy and phenoxy substituents on the alpha carbon atom of a 2-alkoxycarboxylic acid are introduced by appropriate choice of the organic compound having a hydroxyl or thiol group. De-alkoxylation of the 2-alkoxycarboxylic acid yields alpha-beta monoolefinically unsaturated carboxylic acids which are necessarily alpha substituted, and may also be beta-substituted. It is now possible to produce, simply and conveniently, numerous substituted alpha-beta monoolefinically unsaturated carboxylic acids with a variety of substituents on the alpha carbon atom, and, optionally on the beta carbon atom of these substituted carboxylic acids. Esters may also be conventionally derived from both the 2-alkoxycarboxylic acids, and the unsaturated carboxylic acids.

During the phase transfer catalyzed synthesis of this invention, an intermediate acyl halide derivative is formed prior to the formation of the 2-alkoxycarboxylic acid reaction product. The formation of the acyl halide derivative allows the subsequent direct formation, in a modification of the same reaction, of 2-alkoxycarboxylic acid amides (or "2-alkoxycarbamides"), simply by adding a primary or secondary amine to the reaction mass. By dealkoxylation of the 2-alkoxycarbamides, specific, necessarily alpha-substituted and optionally beta-substituted acrylamides are synthesized which previously could be prepared, if at all, only with difficulty.

7 Claims, No Drawings

SYNTHESIS OF ALPHA-ALKOXYCARBOXYLIC ACIDS

BACKGROUND OF THE INVENTION

This invention is related to a novel synthesis of alpha-alkoxycarboxylic acids which, with known technology, could otherwise only be made in the laboratory, usually with considerable difficulty. By the term "alpha-alkoxycarboxylic acids" I refer also to alpha-phenoxycarboxylic acids, alpha-thioalkoxycarboxylic acids, and alpha-thiophenoxycarboxylic acids. This invention is more particularly related to the preparation of beta-substituted alpha-alkoxycarboxylic acids from which can be derived a wide variety of (a) substituted acrylic acids which are both alpha and beta substituted, and (b) substituted acrylamides which are both alpha and beta substituted.

The alpha-alkoxycarboxylic (or "2-alkoxycarboxylic") acids and their esters have been highly regarded for their utility in perfumes and other cosmetics; paints, coatings and impregnants; textiles; and, in the paper industry. The acids and esters have also been used on a laboratory scale, as a starting material for the preparation of various acrylates some of which, if they were commercially available, could provide polymers with a wide range of physical and chemical properties not readily available in available acrylates and methacrylates. As is well known, the physical and chemical properties of polymers of acrylic acid esters and methacrylic acid esters depend to a large degree on the type of alcohol from which the esters are prepared, and, the length of the sidechain. Little is known about the properties of acrylates with substituents on the beta carbon, simply because making compounds with such substituents was impractical. Still less is known about polymers which may be formed from substituted acrylic acids having substituents on both the alpha and beta carbon atoms.

Thus, despite the ability of acrylate and methacrylate esters to copolymerize with nearly all types of monomers, which ability has resulted in extensive industrial use of the esters, the fact remains that, because of the unavailability of all but a few acrylate and methacrylate esters, only the few are presently in wide use. This is so despite the knowledge that some polymers which have more desirable properties for specific applications than poly(methyl methacrylate) ("PMMA") or copolymers of methyl methacrylate and other esters may even be more economical than PMMA. It is undisputed that the bulk availability of only a few substituted acrylates has precluded the commercial exploitation of many novel acrylate-containing polymers, particularly those acrylates with substituents on both the alpha and beta carbon atoms.

In an article titled "The Synthesis of alpha-Alkoxyisobutyric Acids and Alkyl Methacrylates from Acetonechloroform", by Ch. Weizmann, M. Sulzbacher and E. Bergman, *J.A.C.S.* Vol 70, p 1153-1157, there is disclosed a preparation starting with alpha-trichloromethyl alkanol (referred to in the article as 'acetonechloroform', and hereinafter, for brevity, as 'TCMA'), which must first be prepared, and the preparation of which usually entails considerable difficulty. Though once the TCMA is prepared, it readily reacts vigorously with a solution of potassium hydroxide in alkanol, it is acknowledged in the reference that TCMA suffers undefined decomposition to acetone, carbon monoxide, phosgene and formic acid. It is the difficulty of preparing alpha-trichloromethyl alkanol which limits the applicability of the disclosed Weizmann et al reaction to alpha-isobutyric acid. Yet the preparation of the TCMA is critical because the disclosed reaction will not proceed if acetone and chloroform are substituted for the TCMA. It is the difficulty of making and using TCMA which limits its use in the disclosed synthesis to the laboratory.

A phase transfer catalyzed reaction known as the "ketoform reaction" is disclosed in my U.S. Pat. No. 4,167,512, and illustrated in one particular example by the reaction of a N,N'-alkyl substituted ethylene diamine with acetone and chloroform; and, in another example, with o-phenylene diamine reacted with cyclohexanone and chloroform. The reaction product in each example is a 2-keto-1,4-diazacycloalkane. The patented synthesis also proceeds by virtue of a phase transfer catalyzed reaction mechanism in which an amine, a haloform and a ketone are separate reactants, but the patented synthesis does not envision the use, as yet another reactant, of an organic compound having at least one reactive hydroxyl or thiol group.

SUMMARY OF THE INVENTION

It has been discovered that an organic compound having at least one reactive hydroxyl or thiol group, such as alcohols and thioalcohols, phenols and thiophenols will react in a phase transfer catalyzed reaction with a haloform, and a ketone, to yield alpha-alkoxycarboxylic acids. More particularly, the alpha-alkoxycarboxylic acids may be produced with a wide variety of substituents, both on the alpha and the beta carbon atoms, under controlled easily obtained conditions, usually without requiring heating of the reaction mixture.

Accordingly, it is a general object of this invention to provide a simple and convenient synthesis of alpha-alkoxycarboxylic acids including alpha-phenoxycarboxylic acids, and corresponding thioalkoxy carboxylic acids, utilizing commercially available raw materials, which react in the presence of a phase transfer catalyst, and provide excellent yields with a remarkable freedom from undesirable byproducts.

It is also a general object of this invention to provide alpha-alkoxycarboxylic acids which may thereafter be de-alkoxylated to alpha-beta monoolefinically unsaturated carboxylic acids which are necessarily alpha-substituted and optionally, also beta-substituted, and which acids would otherwise be impractical to synthesize.

It is a specific object of this invention to provide a novel synthesis, wherein a preselected primary or secondary alcohol or thioalcohol, phenol or thiophenol, is reacted with a saturated acyclic or cyclic monoketone, and, a haloform, in the presence of (i) a phase transfer catalyst (ii) an organic solvent, and (iii) solid or aqueous alkali. The phase transfer catalyst is selected from the group consisting of a tertiary or quaternary compound of an element selected from Groups VA and VIA of the Periodic Table, and, a polyether. An intermediate acyl halide derivative is formed which then results in an alpha-alkoxycarboxylic acid reaction product. This product is particularly suited for de-alkoxylation to yield an alpha-substituted alpha-beta monoolefinically unsaturated carboxylic acid which may also optionally be beta-substituted.

It is also a specific object of this invention to provide a novel and convenient synthesis, directly, for an alpha-alkoxycarboxylic acid amide (or "2-alkoxycarbamide") by adding a primary or secondary amine to the reactants which, without the amine, would yield a 2-alkoxycarboxylic acid. Because of the formation of an acyl halide intermediate, the amide is formed. In this modification of the phase transfer catalyzed synthesis of this invention, substituents may be introduced on both the alpha and the beta carbons of the substituted acrylamides formed.

DETAILED DESCRIPTION OF PREFERRED EMBODIMENTS

The basic structure of the compounds prepared by the synthesis described herein, is a substituted alpha-alkoxymonocarboxylic acid, formed by reaction of a primary or secondary alcohol or thioalcohol, a phenol or a thiophenol, with a haloform selected from chloroform, bromoform and iodoform, and a cyclic or acyclic monoketone in the presence of a phase transfer catalyst and an alkali, preferably an alkali metal hydroxide. The reaction may be represented as follows:

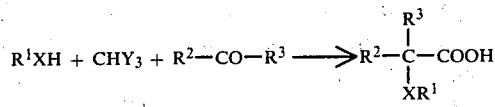

wherein, X represents oxygen or sulfur;

Y represents halogen selected from the group consisting of chlorine, bromine and iodine;

$R^1$, $R^2$ and $R^3$ are independently alkyl having from 1 to about 24 carbon atoms, phenyl, hydroxyphenyl, haloalkyl having from 1 to about 12 carbon atoms, hydroxyalkyl having from 1 to about 12 carbon atoms, cyanoalkyl having from 2 to about 12 carbon atoms, alkoxyalkyl having from 1 to about 24 carbon atoms, cycloalkyl having from 4 to about 7 carbon atoms, or aralkyl having from 7 to about 14 carbon atoms; and, $R^2$ and $R^3$ each additionally represent alkylene having from 2 to about 7 carbon atoms some of which in combination, one with another, represent cycloalkyl having from 5 to about 14 carbon atoms at least four of which are cyclized.

Though the foregoing reaction proceeds with a tertiary alcohol or tertiary thioalcohol, the results are not attractive from a practical point of view. The reaction also proceeds with diols and dithiols, for example 1,2-butanediol and 1,2-benzene diol. Illustrative of particular substituents that may be introduced into the structure of the above-identified alpha-carboxylic acid are:

where $R^1$ and/or $R^2$ and/or $R^3$ is alkyl, examples are methyl, ethyl, n-propyl, n-butyl, t-butyl, n-hexyl, n-octyl, 2-ethylhexyl, n-decyl, n-tetradecyl, n-octyldecyl, and the like;

where $R^1$ is aralkyl, examples are benzyl, and 2-phenylethyl;

where $R^2$ and $R^3$ are combined to form cycloalkyl, examples are tetramethylene, pentamethylene.

Examples of specific substituted alpha-alkoxymonocarboxylic acids derived from readily available starting materials, and prepared by the synthesis of this invention, are:
2-methoxy-2-phenyl propionic acid;
2-ethoxy-2-isobutylpropionic acid;
2-methoxy-2-isobutoxy-4-methyl pentanoic acid;
2-cyclohexylmercapto-isobutyric acid;
2-isobutoxy-methylethyl acetic acid;
2-isobutoxycyclohexane carboxylic acid;
2-isobutoxy-2-ethyl heptoic acid;
2-ethoxy-isobutyric acid; and,
2-dodecoxyisobutyric acid.

The more preferred substituted alpha-alkoxycarboxylic acids are those wherein: $R^1$ and/or $R^2$ and/or $R^3$ is each selected from the group consisting of alkyl having from 1 to 18 carbon atoms, benzyl, cyclohexylmethyl, and polymethylene having from 2 to 6 carbon atoms which are cyclizable.

Examples of the aforespecified more preferred substituted compounds are:
2-methoxyisobutyric acid;
2-methoxycyclohexane carboxylic acid;
2-methoxy-2-methylpentanoic acid;
2-phenoxy isobutyric acid; and,
2-thiophenoxy isobutyric acid.

According to the synthesis of this invention is has been found that phenols, thiophenols, alcohols, and thioalcohols may be reacted with a saturated or unsaturated monoketone and a haloform reactant, in an organic solvent for the reactants, in the presence of aqueous or solid alkali, provided there is also supplied a phase transfer catalyst selected from the group consisting of a polyether and an onium salt including a quaternary or tertiary organic compound of a Group VA or VIA element of the Periodic Table, and salts thereof. More preferred are the tertiary amines, quaternary amines, and salts thereof. The reaction may be carried out at any temperature within a wide range from about the freezing point of the reaction mass to about the reflux temperature of the solvent, provided it is lower than a temperature which is deleterious to the alpha-alkoxycarboxylic acid formed. The reaction is of particular interest because it generally proceeds at room temperature or below, at satisfactory speed, and with excellent yields. The reaction may also be carried out at any desired pressure from subatmospheric to superatmospheric, but atmospheric pressure is preferably employed for convenience, and because there appears to be no substantial advantage to be gained from operating at higher pressures.

By "onium salts" I more particularly refer to tertiary or quaternary amines and salts such as are generally used in the phase transfer catalysis of heterogeneous reactions in immiscible liquids. The general requirement for the onium salt chosen is that it be soluble in both the organic and aqueous phases, when these two liquid phases are present, and usually a little more soluble in the organic phase than the aqueous phase. The reaction will also proceed with a phase transfer catalyst when there is only a single organic liquid phase present, but such a reaction is less preferable than one in which both aqueous and organic liquid phases are present. A wide variety of onium salts is effective in this synthesis.

The onium salts include the well-known salts, tertiary amines and quaternary compounds of Group VA elements of the Periodic Table, and some Group VIA elements such as are disclosed in U.S. Pat. No. 3,992,432 and in a review in Angewandte Chemie, International Edition in English, 16 493–558 (August 1977). Discussed therein are various anion transfer reactions where the phase transfer catalyst exchanges its original ion for other ions in the aqueous phase, making it possible to carry out chemistry there with the transported anion, including $OH^-$ ions.

The onium salts used in this synthesis include one or more groups having the formula $(R_nY)^+X^-$, wherein Y is either a pentavalent ion derived from an element of Group VA, or a tetravalent ion derived from an element of Group VIA; R is an organic moiety of the salt molecule bonded to Y by four covalent linkages when Y is pentavalent, and three covalent linkages when Y is tetravalent; $X^-$ is an anion which will dissociate from the cation $(R_nY)^+$ in an aqueous environment. The group $(R_nY)^+X^-$ may be repeated as in the case of dibasic quaternary salts having two pentavalent Group VA ions substituted in the manner described.

The preferred onium salts for use in the invention have the formula $$(R_1R_2R_3R_4M^+)X^-$$

wherein M is N or P, and $R_1$-$R_4$ are monovalent hydrocarbon radials preferably selected from the group consisting of alkyl, alkenyl, aryl, alkaryl, aralkyl, and cycloalkyl moieties or radicals, optionally substituted with suitable heteroatom-containing functional groups. The onium salts are generally selected to be preferentially less soluble in the less polar of the two distinct liquid phases. Any of the salts disclosed in U.S. Pat. No. 3,992,432 will be found effective, but most preferred are those in which the total number of carbon atoms in $R_1$, $R_2$, $R_3$, and $R_4$ cumulatively range from about 13 to about 57, and preferably range from about 16 to about 30. Most preferred onium salts have M=N, and hydrocarbon radicals where $R^1$ is $CH_3$, and $R^2$, $R^3$, and $R^4$ are each selected from the group consisting of n—$C_4H_5$; n—$C_5H_{11}$; mixed $C_5H_{11}$; n—$C_6H_{13}$; mixed $C_6H_{13}$; $C_6H_5$; $C_6H_5CH_2$; n—$C_8H_{17}$; n—$C_{12}H_{25}$; n—$C_{18}H_{37}$; mixed $C_8$-$C_{10}$ alkyl; and the like. However, $R_1$ may also be selected from $C_2H_5$, n—$C_3H_7$ and n—$C_4H_9$.

Various counterions may be used, including $Cl^-$, $Br^-$, $I^-$, $NO_3^-$, $SO_4^=$, $HSO_4^-$ and $CH_2CO_2^-$. Most preferred is $Cl^-$.

The tertiary amines or triamines useful as phase transfer catalysts in this synthesis include the alkyl amines and the aryldialkylamines, exemplified by tributylamine and phenyldibutylamine respectively, which are commonly available, wherein each alkyl may have from 1 to about 16 carbon atoms.

The polyethers useful as catalysts in this synthesis include cyclic polyethers such as the crown ethers, disclosed in *Agenwandte Chemie,* supra, and ayclic polyethers having the formula $$R—O—R'$$

wherein R and R' are independently alkyl having from 1 to about 16 carbon atoms, or alkyl containing substituted functional groups such as hydroxy, sulfur, amine, ether, etc. Most preferred acyclic polyethers have the formula $$R—(OCH_2CH_2)_rOR''$$

wherein R is alkyl having from 1 to about 16 carbon atoms

R'' is alkyl having from 1 to about 16 carbon atoms, or H, and r is an integer in the range from 0 to about 300. Most preferred are commonly available polyethers such as: tetraethylene glycol dimethyl ether; polyethylene oxide (mol wt about 5000); poly(ethylene glycol methyl ether); 1,2-dimethoxyethane; diethyl ether, and the like.

The organic solvent is preferably one of the reactants but may also be any solvent in which the reactants are soluble. Most preferred are primary alcohols which are also reactants. Other solvents which do not take part in the reaction include hydrohalomethylenes, particularly hydrochloromethylenes, sulfolane, dibutyl ether, dimethyl sulfone, diisopropyl ether, di-n-propyl ether, 1,4-dioxane, tetrahydrofuran, benzene, toluene, hexane, carbon tetrachloride and the like. Most preferred solvents are primary alcohols which enter into the reaction, and, hydrochloromethylenes.

The presence of a haloform, such as chloroform, iodoform or bromoform is essential for the reaction to proceed. Most preferred is chloroform as a necessary reagent, but in combination with the phase transfer catalyst the chloroform may also have a catalytic effect. The precise mechanism or the manner in which the haloform affects the reaction, is not understood. The amount of haloform used does not appear to be critical, at least to initiate the reaction, but it is essential that at least a stoichiometric amount of haloform be used if no ketone is to be left unreacted. Though a small amount of unreacted ketone is not deleterious, it is desirable to employ a slight excess of haloform over the stoichiometric amount indicated, to avoid unreacted ketone. Though an excess, up to about a 50% excess of haloform over stoichiometric may provide acceptable results, more than 50% over stoichiometric is to be avoided because of the formation of undesirable side products. A preferred amount of chloroform is in excess of 20 percent by weight of the reaction mass, and is the haloform most preferred.

Alternatively, a stoichiometric amount of chloroform may be used, and an excess of ketone, generally a large excess. If an alcohol such as methyl alcohol is chosen as a reactant, an excess of the alcohol is used because it also serves as the solvent for the reaction.

If however, instead of a primary alcohol which is a solvent for the other reactants, another organic compound having at least one reactive hydroxyl group is used, and such compound did not function as a solvent for the reactants, at least a stoichiometric amount of the compound is required. Under such circumstances, an inert solvent for the reactants, which solvent does not enter into the reaction, would be used. It will be evident to one skilled in the art that the goal of obtaining the highest yield of the desired reaction product with the minimum amount of undesired byproducts and the greatest economy of raw materials, will require a little trial and error. This reaction being a phase transfer catalyzed reaction, it is difficult to predict with any degree of certainty, precisely how well a reaction will proceed even when it is known that it will certainly proceed.

When an amide is desired, at least a stoichiometric amount of the primary or secondary amine is added, at least a 20% excess being preferred. Preferred substituents for the primary and secondary amines are set forth hereinafter, and the primary amines are most preferred. Unreacted amine does not interfere with the reaction, but too large an excess may give rise to problems in separating the reaction product from the reaction mass.

Though the amount of phase transfer catalyst used is not critical, its catalytic function is unique in this modified ketoform reaction which yields a 2-alkoxycarbamide. In general, it is sufficient to use no more onium salt catalyst than about 2 percent by weight of the reaction mass, and it is preferred to use in the range from about 0.1 to about 1 percent by weight.

The temperature for carrying out both the modified ketoform reactions described hereinabove spans a wide range, whether the reaction, in one form, results in the formation of a 2-alphaalkoxycarboxylic acid, or, in another modified form, results in the formation of a 2-alphaalkoxycarbamide. Best results are obtained at a temperature above the freezing point of the reaction mass and below room temperature (20° C.), melting ice temperature being most preferred.

De-alkoxylation of the 2-alphacarboxylic acids and 2-alphacarbamides obtained may be carried out by heating with an equivalent amount of phosphorus pentoxide, or with oxalic acid, zinc chloride or alcoholic sulfuric acid. Alkoxyacids containing secondary alkyl radicals are especially easily converted into unsaturated compounds, so that obtaining a wide variety of substituents on the alpha carbon, and also, on the beta carbon may now be conveniently accomplished. Conditions for de-alkoxylation are well known in the art and require no further detailed description.

The mono-ketone is preferably saturated and may be cyclic or acyclic. Useful cyclic ketones are those which cyclize forming a cycloalkyl ring. Other ketones are chosen to provide a desired substituent in the alpha-alkoxycarboxylic acid. Most preferred ketones are cycloalkanones, dialkylketones, and aralkylketones.

The preferred alkali is an aqueous alkali metal hydroxide solution such as aqueous sodium hydroxide, or potassium hydroxide, preferably in the range from about 20 percent to about 70 percent solutions. If the alkali metal hydroxide is used in solid form, it is preferably in finely divided powder form typically less than 80 U.S. Standard mesh in size. The amount used is preferably at least three equivalents of alkali metal hydroxide for good progress of the desired reaction. It is preferred to use sufficient aqueous alkali solution to form a visually distinct aqueous phase in the presence of the organic solvent phase. In general, the amount of aqueous alkali used is preferably at least 5 percent by weight of the reaction mass. There is no advantage to using more aqueous alkali than about 75 percent by weight of the reaction mass. It will be appreciated that, if solid alkali is used, it will be a reactant which is soluble in another reactant, or in a solvent for the reactants, only to the extent that it provides necessary $OH^-$ ions for carrying out the phase transfer synthesis.

The following examples serve to illustrate the invention. Where not otherwise stated, parts are given as parts by weight and the temperatures in degrees centigrade.

EXAMPLE 1

Preparation of 2-methoxyisobutyric acid

Methanol (MeOH), chloroform (CHCl$_3$), acetone and benzyltriethylammonium chloride (hereafter "BTAC" for brevity), are placed in a large three-necked flask and cooled in an ice bath. The proportions of MeOH, CHCl$_3$, acetone and BTAC were 32, 23.9, 17.43 and 2.28 parts by weight respectively. While the mixture was being stirred on the ice bath, 56 parts 50% NaOH was added dropwise. About 80% of the NaOH was added over a period of 30 min and the temperature was kept below 9° C., after which the temperature remained at 9° C. for about 20 min. The remainder of the NaOH was added over a period of 10 min and the temperature rose to 16° C. Stirring of the reaction mass was continued overnight, and thereafter the reaction mass was filtered. Solid NaCl precipitated out and was washed with MeOH to free it from desired reaction product, and the 2-methoxyisobutyric acid formed during the reaction is recovered after acidification of the sodium salt, by evaporation of the methanol.

The structure of the compound is confirmed and supported by IR, NMR, GC and mass spectrometer analysis.

In an analogous manner, by choosing the alcohol and the ketone with appropriate substituents, the 2-alkoxycarboxylic acids identified hereinbelow are synthesized. Melting points and boiling points are given.

| Compound | B. pt. or m. pt. |
|---|---|
| 2-methoxycyclohexane carboxylic acid | b. pt. 104–6° C./1.5 mm |
| 2-methoxy-2-methylpentanoic acid | b. pt. 89–92° C./1.5 mm |
| 2-phenoxyisobutyric acid | m. pt. 97–9° C. |
| 2-thiophenoxyisobutyric acid | m. pt. 63–5° C. |

According to a modification of the synthesis of this invention it has also been found that phenols, thiophenols, alcohols, and thioalcohols may be reacted with a primary or secondary amine, a saturated or unsaturated monoketone and a haloform reactant, in an organic solvent for the reactants, in the presence of aqueous or solid alkali, provided there is also supplied a phase transfer catalyst identified hereinabove. The reaction product is a 2-alkoxycarbamide which may be represented by the formula

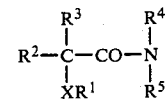

wherein, X represents oxygen or sulfur;

$R^1$, $R^2$, $R^3$, $R^4$ and $R^5$ are independently alkyl having from 1 to about 24 carbon atoms, phenyl, hydroxyphenyl, haloalkyl having from 1 to about 12 carbon atoms, hydroxyalkyl having from 1 to about 12 carbon atoms, cyanoalkyl having from 2 to about 12 carbon atoms, alkoxyalkyl having from 1 to about 24 carbon atoms, cycloalkyl having from 4 to about 7 carbon atoms, or aralkyl having from 7 to about 14 carbon atoms; and, $R^2$ and $R^3$ each additionally represent alkylene having from 2 to about 7 carbon atoms which in combination, one with another, represent cycloalkyl having from 5 to about 14 carbon atoms at least four of which are cyclized.

The formation of the above-identified carbamide is presumed to result from a precursor acyl halide which, but for the presence of the amine, would result in the formation of a 2-alkoxycarboxylic acid. The 2-alkoxycarbamide formed is easily de-alkoxylated by acid elimination of the alkoxy group, as is conventional, to yield a beta-substituted alpha-beta monoolefinically unsaturated carbamide which is also necessarily alpha-substituted. The importance of this synthesis stems from the fact that it is not practical to convert a 2-alkoxycarboxylic acid, once it is formed, into a carbamide.

The preparation of a 2-alkoxycarbamide and its de-alkoxylation is illustrated by Example 2 hereinbelow:

EXAMPLE 2

Preparation of 2-methoxy-N,N'-diethyl-isobutyramide

The reactants used in Example 1 hereinabove are again placed in a 250 ml three-necked flask and one equivalent of diethylamine is added to the flask. The flask is cooled on an ice bath, as before, and the 50% NaOH solution added dropwise. The reaction which occurs may be represented as follows:

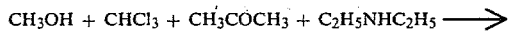

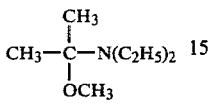

After the reaction is complete, sufficient water is added to dissolve the NaCl crystals formed, and to leave two distinct layers, one aqueous and the other organic. The organic layer is recovered and the 2-methoxy-N,N'-diethylisobutyramide obtained by evaporation of the alcohol.

The structure of the compound is confirmed and supported by IR, NMR, GC and mass spectrometer analysis.

In an analogous manner, by an appropriate choice of a ketone, any of the substituents identified hereinabove may be introduced on the beta carbon atom. The choice of the organic compound having at least one hydroxyl or thiol group is of lesser importance if the alkoxy group on the alpha carbon of the 2-alkoxycarbamide is to be eliminated to produce an alpha- and beta-substituted alpha-beta monoolefinically unsaturated carbamide. This dealkoxylation is effected by simple acidic elimination, by acidifying with sulfuric acid or hydrochloric acid, as is conventional.

As will now be evident, a primary amine will not serve to provide two substituents on the nitrogen atom, therefore secondary amines are most preferred. The following carbamides are prepared by the foregoing procedure:
2-thiophenoxy-N,N'-diethylisobutyramide;
2-thioethoxy-N,N'-dipropylisobutyramide;
2-ethoxy-N,N'-dibutylcyclohexane carbamide;
2-methoxy-2'-phenoxy-N,N'-diethylpropionamide; and,
2-methyl-2-phenoxy-N-methyl,N'-phenyl-butyramide.

I claim:

1. A method for preparing an alpha-alkoxycarboxylic acid, or alpha-thioalkoxycarboxylic acid, comprising reacting an organic compound selected from the group consisting of alcohols, thioalcohols, phenols and thiophenols with a cycloalkanone, dialkylketone or aralkylketone in the presence of (i) a haloform, (ii) alkali metal hydroxide, and (iii) a phase transfer catalyst selected from the group consisting of tertiary and quaternary compounds of Group VA and Group VIA elements, and, a polyether, said phase transfer catalyst being present in an amount sufficient to form a salt of said alpha-alkoxycarboxylic acid or alpha-thioalkoxycarboxylic acid; forming said alpha-alkoxycarboxylic acid or alpha-thioalkoxycarboxylic acid by acidifying said salt; and, recovering said alpha-alkoxycarboxylic acid or alpha-thioalkoxycarboxylic acid.

2. The method of claim 1 including, in addition, dealkoxylating said alpha-alkoxycarboxylic acid or alpha-thioalkoxycarboxylic acid; and, recovering an alpha-substituted alpha-beta monoolefinically unsaturated carboxylic acid which optionally is also beta-substituted.

3. The method of claim 1 wherein said alpha-alkoxycarboxylic acid or alpha-thioalkoxycarboxylic acid is represented by the structural formula

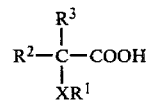

wherein, X represents oxygen or sulfur;
$R^1$, $R^2$ and $R^3$ are independently alkyl having from 1 to about 24 carbon atoms, phenyl, hydroxyphenyl, haloalkyl having from 1 to about 12 carbon atoms, hydroxyalkyl having from 1 to about 12 carbon atoms, cyanoalkyl having from 2 to about 12 carbon atoms, alkoxyalkyl having from 1 to about 24 carbon atoms, cycloalkyl having from 4 to about 7 carbon atoms, or aralkyl having from 7 to about 14 carbon atoms; and,
$R^2$ and $R^3$ each additionally represent alkylene having from 2 to about 7 carbon atoms which in combination, one with another, represent cycloalkyl having from 5 to about 14 carbon atoms at least four of which are cyclized.

4. The method of claim 3 including maintaining a temperature above the freezing point of the reaction mass but below the reflux temperature of the solvent, and, adding said haloform in a slight excess over the stoichiometric amount required to react essentially all of said monoketone.

5. The method of claim 4 wherein X is oxygen, and $R^1$, $R^2$ and $R^3$ are independently selected from said alkyl, cycloalkyl, aralkyl and phenyl.

6. A method for preparing an alpha-alkoxycarboxylic acid, or alpha-thioalkoxycarboxylic acid, represented by the structural formula

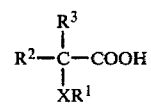

wherein, X represents oxygen or sulfur;
$R^1$, $R^2$ and $R^3$ are independently alkyl having from 1 to about 24 carbon atoms, hydroxyphenyl, haloalkyl having from 1 to about 12 carbon atoms, hydroxyalkyl having from 1 to about 12 carbon atoms, cyanoalkyl having from 2 to about 12 carbon atoms, alkoxyalkyl having from 1 to about 24 carbon atoms, cycloalkyl having from 4 to about 7 carbon atoms, or aralkyl having from 7 to about 14 carbon atoms; and,
$R^2$ and $R^3$ each additionally represent alkylene having from 2 to about 7 carbon atoms which in combination, one with another, represent cycloalkyl having from 5 to about 14 carbon atoms at least four of which are cyclized, comprising,
reacting an organic compound having at least one reactive hydroxyl or thiol group with a monoketone in the presence of (i) a haloform, (ii) alkali, and (iii) a phase transfer catalyst selected from the group consisting of tertiary and quaternary compounds of Group VA and Group VIA elements, and, a polyether, said phase transfer catalyst being present in an amount sufficient to form said alpha-alkoxycarboxylic acid or alpha-thioalkoxycarboxylic acid;

recovering said alpha-alkoxycarboxylic acid or alpha-thioalkoxycarboxylic acid;

dealkoxylating said alpha-alkoxycarboxylic acid or alpha-thiocarboxylic acid; and, forming an alpha-beta monoolefinically unsaturated carboxylic acid which is alpha-substituted, and represented by the structural formula $$R^2=\underset{\underset{R^3}{|}}{C}-COOH$$

7. The method of claim 6 wherein $R^2$ and $R^3$ are independently selected from said alkyl, aralkyl, and cycloalkyl.

* * * * *